United States Patent [19]

Strand

[11] Patent Number: 4,938,773

[45] Date of Patent: Jul. 3, 1990

[54] HIP JOINT PROSTHESIS

[76] Inventor: John A. Strand, 34 Strathallan Park, Rochester, N.Y. 14607

[21] Appl. No.: 298,166

[22] Filed: Jan. 18, 1989

[51] Int. Cl.⁵ .............................................. A61F 2/32
[52] U.S. Cl. ..................................................... 623/23
[58] Field of Search ...................... 623/16, 18, 20, 22, 623/23

[56] References Cited

U.S. PATENT DOCUMENTS 4,177,524  12/1979  Grell et al. ............................ 623/18
4,693,724   9/1987  Rhenter et al. ....................... 623/23

FOREIGN PATENT DOCUMENTS 0290735  11/1988  European Pat. Off. .............. 623/23
2621666  11/1977  Fed. Rep. of Germany ........ 623/22
2575383   7/1986  France ................................... 623/18

*Primary Examiner*—David J. Isabella
*Attorney, Agent, or Firm*—Richard C. Litman

[57] ABSTRACT

A total hip joint prosthesis with primary fixation includes a partially threaded elongated pin for insertion into the femoral body to provide primary support for the prosthesis. Attachable thereto is a proximal body whose shape simulates the proximal medial region on the femur and provides a neck for the attachment of a head to contact the acetabulum. The components are constructed to allow for relative rotational adjustment between the body and the pin, thus providing for various alignments and size combinations to offer a custom fit in view of the individual patient's needs. A tapered bore through the body member receives a threaded mounting post on the pin while a nut having a tapered bottom portion seats within the bore to secure the components in a fixed manner.

4 Claims, 1 Drawing Sheet

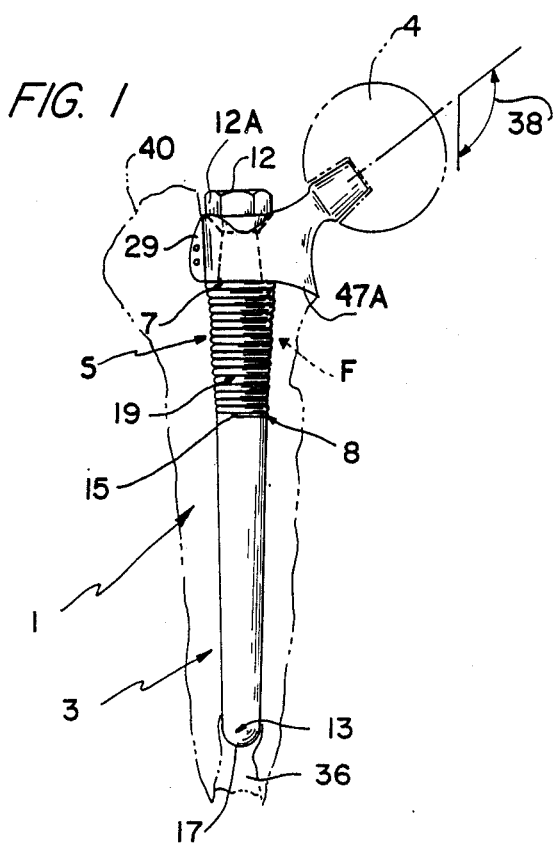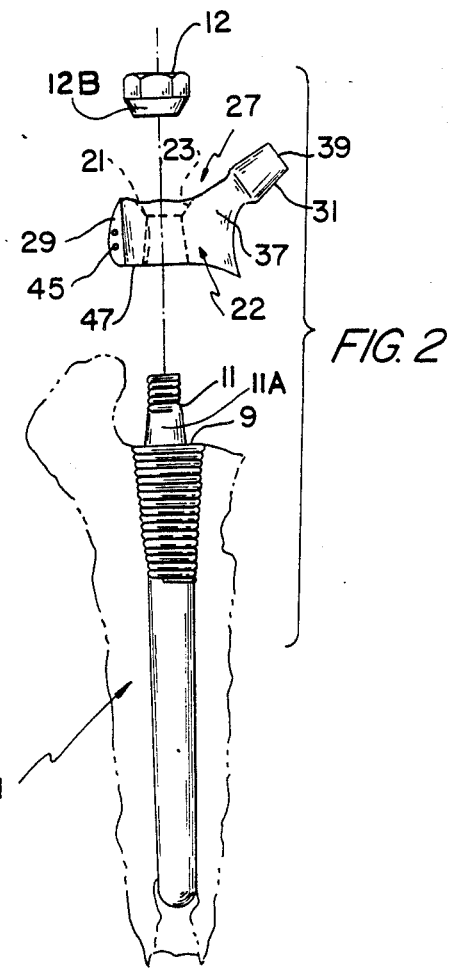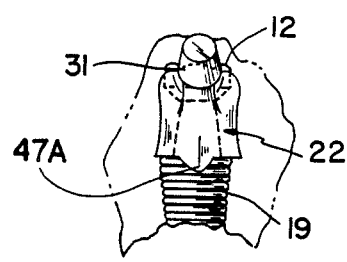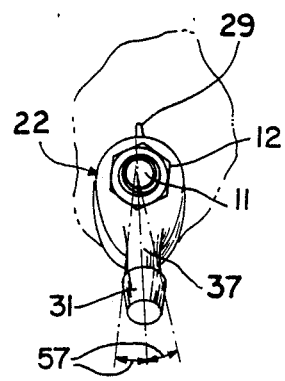

HIP JOINT PROSTHESIS

FIELD OF THE INVENTION

This invention relates generally to surgically implanted prostheses and, in particular, an improved total hip joint prosthesis providing primary fixation.

BACKGROUND OF THE INVENTION

Although hip joint prostheses are generally well-known, those with primary fixation prove to be superior to prostheses whose fixation is achieved through an adhesive means.

Primary fixation provides a fixation in which through some mechanical means the prosthesis is fixed in the bone. The aforementioned mechanical means essentially displaces areas of the bone and requires the bone to grow around the implant, thus securing the implant.

In the past, solutions to the best means of primary fixation have shown threaded pins and also "nails" for insertion into the femoral body. These procedures, while each has merit, do not provide an adequate solution to such problems as postoperative patient discomfort and providing for size adjustment and alignment to best suit the patients needs.

DESCRIPTION OF RELATED ART

As an example, a threaded pin for insertion into the medullar cavity of the femur is proposed in U.S. Pat. No. 4,693,724. A pin has a constant thread depth and the threading includes notches to facilitate the implantation. While such construction provides great advantages over the previously known "nails", the design is lacking in that the notches which provide for ease of implantation traumatize the bone causing postoperative pain and discomfort. Further, the construction does not provide for resistance to rotational forces which are present when in use.

SUMMARY OF THE INVENTION

By the present invention, an improved hip joint prosthesis with primary fixation is provided. The invention contemplates a total hip prosthesis which will be utilized as a permanent long-term replacement for the physiological hip joint. The prosthesis will be biologically fixed in the operating room as a permanent implant. It is desired that the improvement the present invention offers over existing prostheses will provide a means for biological fixation and though its usage increased patient comfort for the life of the implant. Also, the modular design of the invention provides for universal usage on patients with far-ranging size requirements and needs.

Accordingly, one of the objects of the present invention is to provide an improved hip prosthesis with primary fixation whose modularity provides for a plurality of combinations by using components of varying size and therefore virtually universal application.

Another object of the invention is to provide an imitation of the physiological features of the proximal medial femur, thereby allowing the patient a more pain-free use and long-term fixation of the prosthesis.

In addition, an object of the invention is a construction which can be seen to encourage and even enhance conservation of the bone in the area of the implantation.

A further object of the invention is to provide means to facilitate insertion and, if necessary, removal of the prosthesis by a tapered pin and by the varying thread depth on said tapered pin.

Additionally, an object is to provide for relative angular alignment of the opposing planar surfaces of both the pin and attachable body. Moreover, a minimization of the rotational forces which act upon the prosthesis is desired.

With these and other objects in view which will more readily appear as the nature of the invention is better understood, the invention consists in the novel combination and arrangement of parts hereinafter more fully described, illustrated and claimed, with reference being made to the attached drawings.

BRIEF DESCRIPTION OF THE DRAWINGS

FIG. 1 is a side elevation view of the prosthesis in use;

FIG. 2 is a side elevation view of the exploded prosthesis,

FIG. 3 shows the fragmentary front elevation view of the prosthesis; and

FIG. 4 shows the top plan view of the prosthesis.

Similar reference characters designate corresponding parts throughout the several figures of the drawings.

DESCRIPTION OF THE PREFERRED EMBODIMENT

The invention is comprised of three modular components: a elongated component which is a partially threaded pin 1 providing for fixture of the prosthesis to the femur F. A proximal component 29 comprises a proximal body 27 having an angular neck 31 which provides for fixture to the pelvis by means of a head 39 which provides direct contact of the prosthesis to the pelvis. The various components may be constructed in a variety of sizes to provide a custom fit for any one patient. Both the distal pin 1 and the proximal body 27 constructed from titanium.

The distal pin 1 includes an elongated, tapered shank adapted to be inserted into the femoral body F. The outer surface of the shank comprises a lower, smooth portion 3 having an outer surface joined to an upper portion 5 provided with threads 19. The threads 19 provide a positive displacement from the tapered profile of the shank. The threading of the shank commences at the head 7 of the shank, at its largest diameter. This area also presents an upwardly facing transverse planar surface 9 from which an upstanding, inwardly tapered, threaded mounting post 11 projects and which ultimately will receive and retain the proximal body 22. The base 13 of the pin shank will be seen to be rounded as at 17, to facilitate ease of insertion within the central cavity 36 of the femur F.

The pin 1 is tapered along its entire length at a substantially consistent variance of the pin radius from its head 7 to the base 17. This radius ranges from its greatest, at the head 7 of the shank, to its smallest point at the opposite end which is the farthest point of insertion into the femur. The profile of the pin has a substantially constant slope as can be seen in FIGS. 1 and 2. The taper of the thread coincides with the taper of the shank in that as the cross-sectional area of the shank decreases so does the depth of the threads 19.

The threads 19 of the shank provide for the rigid attachment and securing of the pin 1 in the femur F. The thread depth varies uniformly along the entire length of the threaded region 19. This thread depth ranges from 2 millimeters at its deepest point adjacent the pinhead 7 to its shallowest point 8 of 0.5 millimeters intermediate the shank length. In FIG. 1 the profile of the thread is shown to be consistently sloped. The tapering of the thread depth will provide a means for self-tapping and ease in insertion and removal of the pin should removal become necessary. The thread has a substantially trapezoidal cross section and rounded edges. The shape of the threads and their inherent taper will eliminate patient discomfort and pistoning which may occur between the threads and its contact inside the femorral body upon insertion therein.

The mounting post 11 and adjacent planar head surface 9 of the pin provide for the positive attachement of the proximal body 27 which will be seen to include a vertical passageway comprising a lower bore 21 adjacent an enlarged, outwardly tapered upper bore 23. The thread of the mounting post freely passes through the lower bore 21 and similarly clears the upper bore 23 as shown in FIGS. 1 and 2, with the lower unthreaded and tapered portion 11A of the post closely seating within the head lower bore 21. With the body 27 atop the pin 1, the undersurface 47 thereof smoothly abuts the surface 9 of the pin head and surrounding femur. The body undersurface 47 includes a depending outer wing or edge 47A preferably forming a V shape as shown in FIG. 3, and is adapted to provide an interlock against angular displacement when embedded within the femur. The proximal body 22 is secured by means of a threaded fastener 12 in the form of a nut or the like serving to lock the pin and body together in their desired angular alignment for permanent fixation. The nut head 12A is preferably polygonal to facilitate application by a suitable tool and includes a bottom tapered portion 12B substantially mating with the body upper bore taper 23. The surface 9 of the head of the pin and the undersurface 47 of the bases of the body are microgrooved so as to increase the coefficient of friction between the two components and thus prevent slippage when the fastener 12 is tightened upon the post 11. During this tightening, the taper 12B of the nut 12 will be understood to provide a self-centering of the body 27 as the nut taper progressively seats against the body upper bore 23.

The proximal body 27 imitates the shape of the proximal medial area of the physiological femur. This body provides planar contact with the area of the femur between the greater and lesser trochanter. The body may be viewed in sections for better understanding of its structure and function although it is an integral unit. The body includes a neck section 31 which extends at an upward angle from the base section and has at its free end the head 39 which is the means through which direct contact with the acetabulum 4 is achieved. This head 39 provides a frustoconical configuration 31.

The base of the body will thus be understood to include an underside, a sidewall and the remainder of the perimeter which simulates the area of the physiological femur that it is replacing. The underside 47 forms an opposing face which provides for contact with the head 7 of the pin 1 and contacts the proximal area of the lesser trochanter while the sidewall forms contact with the medial area of the greater trochanter. Additional load-bearing is provided by the body through its contact surface area of the underside. The contact surface distributes stress peaks between the prosthesis and the bore contact points 21, 23 which receives the mounting means from the head of the pin. The bore 21,23 is of sufficient diameter to accommodate the mounting means while also providing a recessed bore of sufficient diameter to receive the fastening means. In providing a recessed bore for the insertion of the fastening means, the outline of the base will be contoured so as to eliminate the exposure of both the mounting and fastening means.

The body neck 37 will be seen to extend upwardly and outwardly at an acute angle from the plane formed by the underside 47. This neck provides for the attachment of the head 39 at the end opposite the base 22 and defines a substantially frustoconical configuration with its largest diameter at its base adjacent to the neck 37. Provision may be made for the mounting of the head 4 on the neck 31, 39 at various angles to accommodate the patient's need and to provide the best fit.

The proximal body is designed to provide certain means for preventing rotation after fixation is achieved. As described above, the underside 47 is microgrooved to prevent slippage while in contact with the pin. Also provided is a trochanteric wing 29 projecting radially from the sidewall, opposite the side from which the neck 37 extends. The wing 29 provides further anchoring within the area 40 of the femur for the prosthesis after fixation is achieved. The wing 29 is provided with holes 45 to facilitate the wiring of the wing to the femur bone area F for additional rotation prevention.

The construction of the distal pin in conjunction with the construction of the proximal component provide the possibility of a plurality of mounted positions with respect to each other, and the selected position will be positively retained in view of the grooved underside of the body and top of the pin.

The neck portion 37 and its head will be understood to be angularly disposed substantially between 130–150 degrees with respect to the vertical, central axis of the pin 1, as represented by the angle 38 in FIG. 1. The taper 31 of the neck head 39 will be readily apparent in view of FIG. 2. Additionally, the anteversion and retroversion that the modular prothesis is capable of is readily shown by 57 in FIG. 4.

It is to be understood that the present invention is not limited to the sole embodiment described above, but encompasses any and all embodiments within the scope of the following claims.

I claim:

1. A hip joint prosthesis comprising:
an elongated distal pin of circular cross section having a tapered shank including an upper threaded portion and a lower portion, said threaded portion extending along said shank from a proximal threaded end distally to a distal threaded end adjacent said lower unthreaded portion, said threaded portion including threads of substantially trapezoidal cross-section varying uniformly in pitch from the proximal threaded end to the distal threaded end.

a mounting post projecting upwardly from said proximal threaded portion, said mounting post having secondary threading.

a proximal body having a base and a neck member, said neck member forming an angle with said shank and extending medially from said base in imitation of the physiological femur, said base having a vertical through bore formed therein adapted to surround said mounting post, said vertical through bore includes a lower bore adjacent an upper tapered bore, said proximal body having a wing laterally projecting from said base diametrically opposed relative to said neck member and contacting the greater trochanter of the femur, said wing has a plurality of apertures disposed therethrough for wiring said wing to said femur.

said proximal body having a lower surface adapted to seat on a resected surface of the femur, said lower surface having a curved V-shaped protrusion extending medially and downwardly below said neck member to cover the lesser trochanter and is adapted to provide an interlock against angular displacement of the body when embedded within the femur, fastening means engaging said mounting post and adapted to securely affix and proximal body to the femur, said fastening means comprising a threaded nut having a bottom tapered portion providing for centering of said bore in relation to said mounting post, said proximal body having a joint head affixed to said neck portion for engagement with the acetabulum.

2. A hip joint prosthesis according to claim 1 wherein,
said pin defines a substantially frustoconical configuration and a terminal distal end of said lower portion is rounded.

3. A hip joint prosthesis according to claim 1 wherein,
said pin and said body are manufactured of titanium.

4. A hip joint prosthesis according to claim 1 wherein,
said angle between the neck member and the shank is substantially between 130–150 degrees.

* * * * *